US007013573B2

(12) United States Patent
Kinoshita et al.

(10) Patent No.: US 7,013,573 B2
(45) Date of Patent: Mar. 21, 2006

(54) HOLE CENTER DETECTING APPARATUS, STRAIGHTNESS MEASURING APPARATUS, AND RESIDUAL TORSION MEASURING APPARATUS

(75) Inventors: Takashi Kinoshita, Tochigi-ken (JP); Yoshiki Mizuta, Tochigi-ken (JP); Takahiro Yamada, Tochigi-ken (JP); Shogo Ueda, Tochigi-ken (JP); Eiji Kudo, Tochigi-ken (JP); Yuichi Kimura, Tochigi-ken (JP); Yukio Sangawa, Saitama-ken (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 10/423,973

(22) Filed: Apr. 28, 2003

(65) Prior Publication Data

US 2003/0204964 A1   Nov. 6, 2003

Related U.S. Application Data

(62) Division of application No. 09/955,172, filed on Sep. 19, 2001, now Pat. No. 6,578,280.

(30) Foreign Application Priority Data

| Sep. 20, 2000 | (JP) | ............................. 2000-285821 |
| Sep. 20, 2000 | (JP) | ............................. 2000-285822 |
| Sep. 20, 2000 | (JP) | ............................. 2000-285823 |

(51) Int. Cl.
  *G01B 21/22* (2006.01)
(52) U.S. Cl. ........................... 33/533; 33/552; 156/117
(58) Field of Classification Search .................. 33/533, 33/549, 551, 552, 555, 626, 628, 630, 640, 33/750, 751; 156/117
See application file for complete search history.

(56) References Cited

U.S. PATENT DOCUMENTS

| 3,110,112 | A | * | 11/1963 | Dalgleish ...................... 33/552 |
| 3,307,267 | A | | 3/1967 | Barr et al. |
| 3,470,739 | A | * | 10/1969 | Ishida et al. ................... 73/159 |
| 3,554,249 | A | * | 1/1971 | Arnelo et al. ............... 144/357 |
| 3,994,058 | A | | 11/1976 | Sasaki et al. |
| 4,026,031 | A | | 5/1977 | Siddall et al. |
| 4,026,483 | A | | 5/1977 | Skalleberg |
| 4,050,293 | A | * | 9/1977 | Shimomura et al. .......... 73/105 |
| 4,386,344 | A | | 5/1983 | Vecchiatto |
| 4,589,082 | A | * | 5/1986 | Parker et al. ................ 702/135 |
| 4,647,208 | A | | 3/1987 | Bieman |
| 4,652,744 | A | * | 3/1987 | Bowers et al. .............. 250/227 |
| 4,785,675 | A | * | 11/1988 | Takasu et al. ............ 73/862.33 |
| 5,205,046 | A | * | 4/1993 | Barnett et al. ................ 33/533 |

(Continued)

FOREIGN PATENT DOCUMENTS

CA    2 242 179 A1    1/1999

(Continued)

*Primary Examiner*—Christopher W. Fulton
*Assistant Examiner*—Tania Courson
(74) *Attorney, Agent, or Firm*—Sughrue Mion, PLLC

(57) ABSTRACT

A hole center detecting apparatus for positioning the hole of a spool and a cord accurately by determining the coordinates of two points of intersection between the inner circumference of the spool hole and a virtual straight line to compute the coordinates of the center of the hole and by moving the cord according to the computed coordinates of the hole center. A straightness measuring apparatus for measuring the curvature of a cord automatically by detecting the coordinates of three longitudinal points of the cord. A measurement apparatus for measuring a residual torsion automatically by measuring the rotation angle of the end portion of the cord before and after clamped, electrically.

3 Claims, 16 Drawing Sheets

U.S. PATENT DOCUMENTS

| | | | |
|---|---|---|---|
| 5,214,947 A * | 6/1993 | Sissala et al. ............... 72/17.3 |
| 5,264,918 A | 11/1993 | Kagami | |
| 5,460,333 A | 10/1995 | Vanhuyse | |
| 5,519,944 A * | 5/1996 | Delastre ....................... 33/533 |
| 5,639,506 A * | 6/1997 | Smyth ....................... 427/2.31 |
| 5,771,309 A | 6/1998 | Yamaoka et al. | |
| 5,829,705 A | 11/1998 | Carlberg | |
| 5,886,775 A * | 3/1999 | Houser et al. ............. 356/4.01 |
| 6,354,013 B1 * | 3/2002 | Mucke et al. ................. 33/533 |
| 6,668,626 B1 * | 12/2003 | Grefve et al. ................. 73/104 |
| 6,711,828 B1 * | 3/2004 | McCune et al. ............... 33/533 |

FOREIGN PATENT DOCUMENTS

| | | | |
|---|---|---|---|
| JP | 05-113315 A | | 5/1993 |
| JP | 405180642 A | * | 7/1993 |
| JP | 07-225843 A | | 8/1995 |
| JP | 08159750 A | * | 6/1996 |
| SU | 1087368 A | * | 4/1984 |

* cited by examiner

F I G. 3A
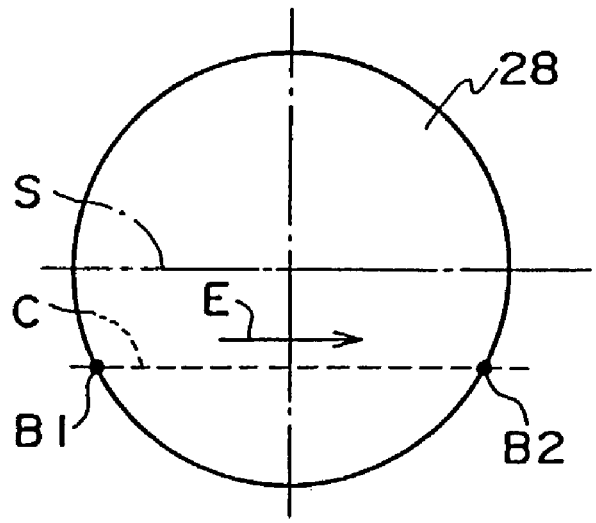
F I G. 3B
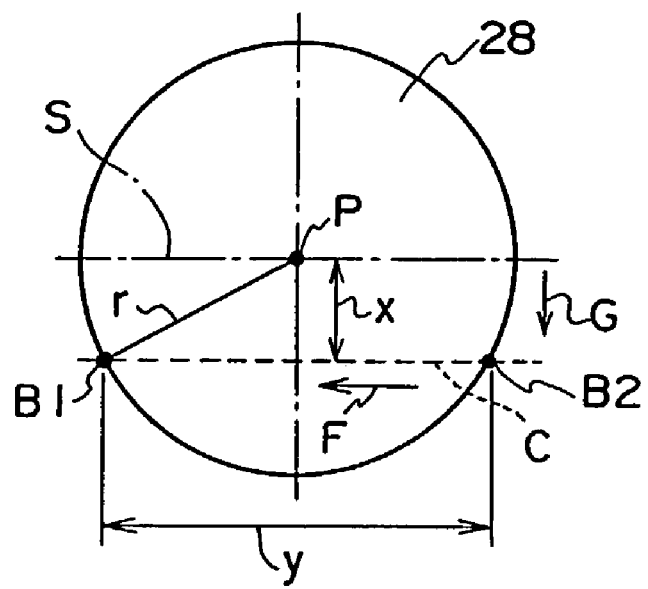

FIG. 10

$$Y_{AB} = -\frac{Bx-Ax}{By-Ay} X_{AB} + \frac{By^2-Ay^2+Bx^2-Ax^2}{2\times(By-Ay)} \quad \cdots \cdot \text{EQUATION(1)}$$

$$Y_{BC} = -\frac{Cx-Bx}{Cy-By} X_{BC} + \frac{Cy^2-By^2+Cx^2-Bx^2}{2\times(Cy-By)} \quad \cdots \cdot \text{EQUATION(2)}$$

$$X = \frac{1}{2} \times \left(\frac{Cy^2-By^2+Cx^2-Bx^2}{Cy-By} - \frac{By^2-Ay^2+Bx^2-Ax^2}{Bx-Ax}\right) \bigg/ \left(\frac{Cx-Bx}{Cy-By} - \frac{Bx-Ax}{By-Ay}\right)$$

$$\cdots \cdot \text{EQUATION(3)}$$

$$Y = -\frac{Bx-Ax}{By-Ay} X + \frac{By^2-Ay^2+Bx^2-Ax^2}{2\times(By-Ay)} \quad \cdots \cdot \text{EQUATION(4)}$$

$$\rho = \sqrt{(X-Ax)^2 + (Y-Ay)^2} \quad \cdots \cdot \text{EQUATION(5)}$$

$$H = \rho \times (1 - \cos\theta/2), \quad \theta = L/\rho \quad \cdots \cdot \text{EQUATION(6)}$$

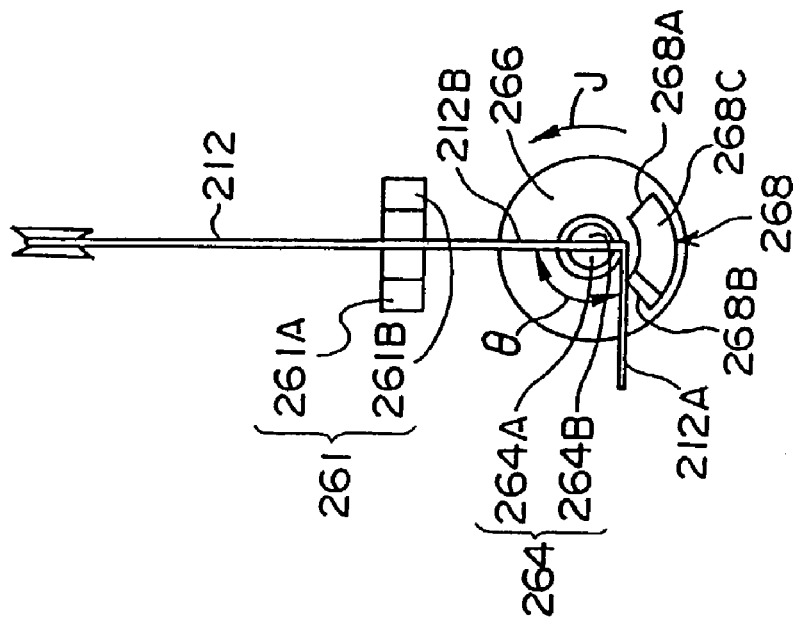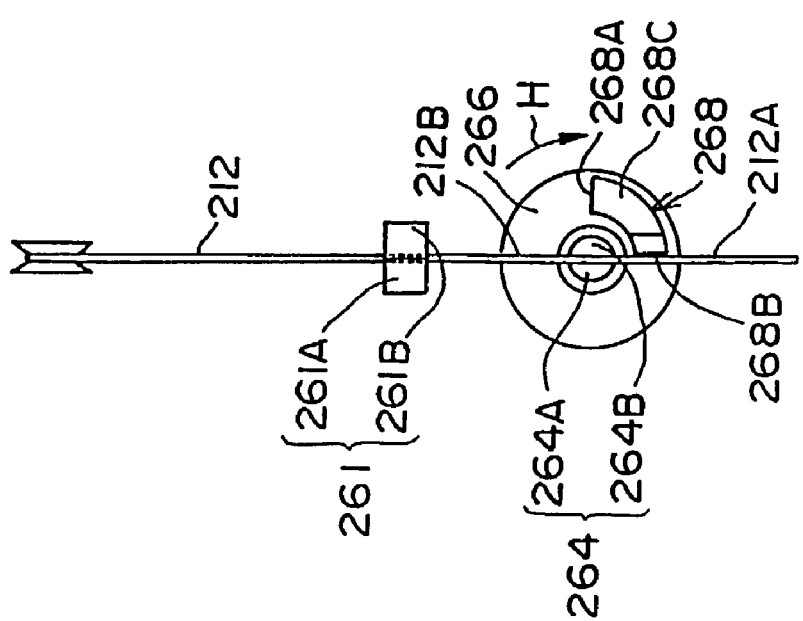

HOLE CENTER DETECTING APPARATUS, STRAIGHTNESS MEASURING APPARATUS, AND RESIDUAL TORSION MEASURING APPARATUS

This is a divisional application based on Ser. No. 09/955,172 filed Sep. 19, 2001 now U.S. Pat. No. 6,578,280, the entire disclosure of which is incorporated herein by reference.

BACKGROUND OF THE INVENTION

1. Field of the Invention

The present invention relates to a hole center detecting apparatus which can be employed when a wire such as a steel cord for reinforcing a rubber part is wound onto a spool which is a member having a hole. Further, the present invention relates to a straightness measuring apparatus for measuring the straightness of a wire such as a steel cord for reinforcing a rubber part automatically. Still further, the present invention relates to a residual torsion measuring apparatus for measuring the residual torsion of a wire such as a steel cord for reinforcing a rubber part automatically.

2. Description of the Related Art

Prior Art 1:

In the working of the prior art for winding a steel cord for reinforcing a rubber part on a spool (as also called a "reel" or "bobbin") having an insertion hole, the cord is wound on the spool after a worker inserts its leading end into the insertion hole by visually identifying the insertion hole.

For this automation for improving the production yield, it is necessary to detect the center of the insertion hole automatically with high precision. For example, employing an apparatus for detecting the center position of the hole by locating the hole with a CCD camera and by processing the graphic digital signals with a computer to extract the shape of the hole and to detect the center position of the hole, is conceivable.

However, since this apparatus employs a CCD camera it is disadvantageous in that the total cost is high. In order to eliminate this disadvantage, it is also conceivable to employ a reflection or transparent type optical sensor which has a lower cost than the CCD camera, and thereby to detect the hole directly. However, it is difficult for this apparatus to detect the center position of the hole with high precision.

Prior Art 2:

In the prior art, the curvature (or straightness) per unit length of the steel cord for reinforcing a rubber part such as a steel cord to be used in a pneumatic tire is controlled so as to ensure workability in the tire manufacturing process. Thus at the final step of the steel cord manufacturing process, the straightness is inspected visually by the inspector using an inspection plate.

However, the visual inspection by the inspector involves problems with respect to precision and deterioration in productivity due to the time required for the inspection.

Prior Art 3:

In the steel cord for reinforcing a rubber part of the prior art such as the steel cord to be used in the pneumatic tire, the residual torsion per unit length is specified in order to ensure the workability in the tire manufacturing process. At the final step of the steel cord manufacturing process, therefore, the residual torsion is measured by an inspector having technical ability at or above a predetermined level, and its value is recorded on a check sheet. When the residual torsion is measured, however, the end portion of an object to be measured is bent. Therefore, there may be some variation in the measurement by the inspector of the length or the angle of the same cord when the end portion is bent. This causes some amount of variation with respect to the precision of the residual torsion measurement.

Measurement and inspection of residual torsion in steel cord manufacturing is essential for ensuring workability in tire manufacturing. At the final step of the steel cord manufacturing process, therefore, the residual torsion is measured and inspected exclusively by an inspector who is qualified by a technical institution and thereby has technical ability that is at or above a predetermined level. However, because the residual torsion is always measured at the final step, the productivity tends to deteriorate. In order to maintain precision in the residual torsion measurement, it was necessary to spend a long time training the inspectors to make them qualified, and it was also necessary to check the precision of their measurements periodically even after they became qualified.

Moreover, the residual torsion may be read in either the "plus" or "minus" direction, depending on the kind of steel cord or test standards (e.g., JIS or ASTM) of the steel cord. Therefore, the inspector has to record the direction of the residual torsion according to the kind of the steel cord or the test standards used by the tire manufacturing factory. Therefore, even a qualified inspector may erroneously record the wrong "plus" and "minus" directions for the different steel cord kinds or test standards.

SUMMARY OF THE INVENTION

In view of the above-mentioned facts, the present invention has an object to provide a hole center detecting apparatus capable of detecting the center of a hole with high precision and at a low cost.

Another object of the present invention is to provide a straightness measuring apparatus capable of measuring the straightness highly precisely and improving the productivity.

Considering the aforementioned facts, still another object of the present invention is to provide a residual torsion measuring apparatus capable measuring the residual torsion highly precisely and improving the productivity.

According to a first aspect of the present invention, there is provided a hole center detecting apparatus comprising: an object having a round hole; coordinate detecting means for detecting the coordinates of two points at which the inner circumference of said hole and a virtual straight line intersect; and coordinate computing means for computing the coordinates of the center of said hole from the detected coordinates of the two points.

According to another aspect of the present invention, there is provided a straightness measuring apparatus comprising: coordinate detecting means for detecting three different coordinates in the longitudinal direction of an object to be measured; straightness computing means for computing the straightness of said object from the curvature of a curve passing through the three points detected by said coordinate detecting means; and display means for displaying the result of the computations made by said straightness computing means.

According to still another aspect of the present invention, there is provided an apparatus for measuring the residual torsion of an object to be measured, the object having a straight portion and a terminal portion bent at a specified angle from one end of said straight portion, and comprising: chuck means for chucking the other end of the straight portion of the object in a releasable manner; and detection means for electrically detecting the angle of the terminal portion of the chucked object with respect to the axis of the straight portion and the angle of the terminal portion of the released object with respect to the same axis.

BRIEF DESCRIPTION OF THE DRAWINGS

FIG. 3A is a diagram showing a detection point in the embodiment shown in FIG. 1.

FIG. 3B is a diagram showing relationship between the detection point and the hole center in the embodiment shown in FIG. 1.

FIG. 10 illustrates several calculation formulas relating to the present invention.

FIGS. 15A and 15B are diagrams showing the cords before and after being bent by the bending unit shown in FIG. 14.

DETAILED DESCRIPTION OF THE PREFERRED EMBODIMENTS

<<Hole Center Detecting Apparatus>>

Figure 1:
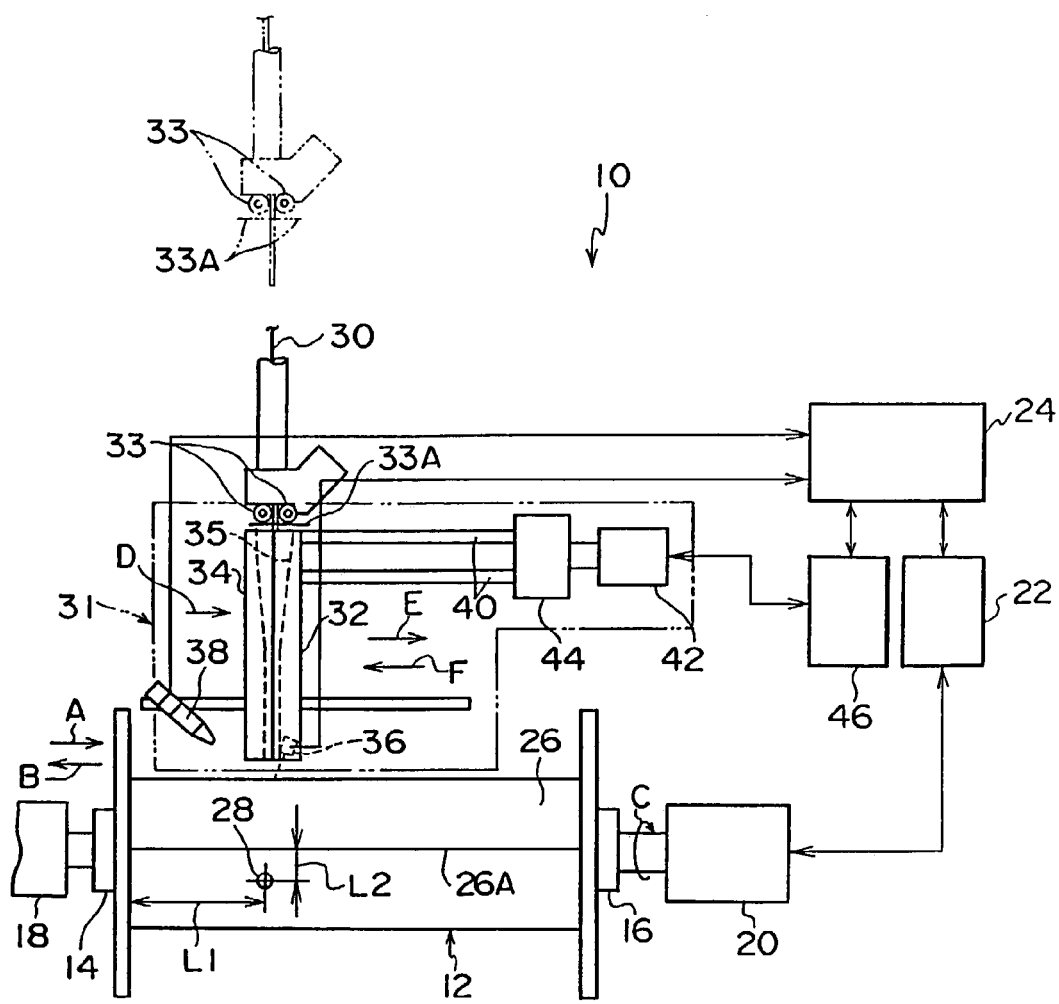
FIG. 1 is a schematic construction diagram showing one embodiment of a hole center detecting apparatus according to the present invention.

First of all, a cord wind-up unit of one embodiment of a hole center detecting apparatus according to the present invention will be described in detail with reference to FIG. 1 to FIGS. 3A and 3B.

A cord wind-up unit 10 is provided with a pair of left and right spool holding arms 14 and 16 for holding a spool 12 on the two axial sides. One holding arm 14 is enabled by moving means (e.g., an air cylinder) 18 to move in a direction (as indicated by arrow A of FIG. 1) to clamp the spool 12 and in a direction (as indicated by arrow B of FIG. 1) to release the spool 12 from the clamped state. The holding arms 14 and 16 are enabled by a take-up servomotor 20 to rotate the held spool 12 on the axis (i.e., in the direction of arrow C of FIG. 1 or backward).

The take-up servomotor 20 is electrically connected through a servomotor driver 22 with a control device (or coordinate computing means) 24 having a computer.

Figure 2:
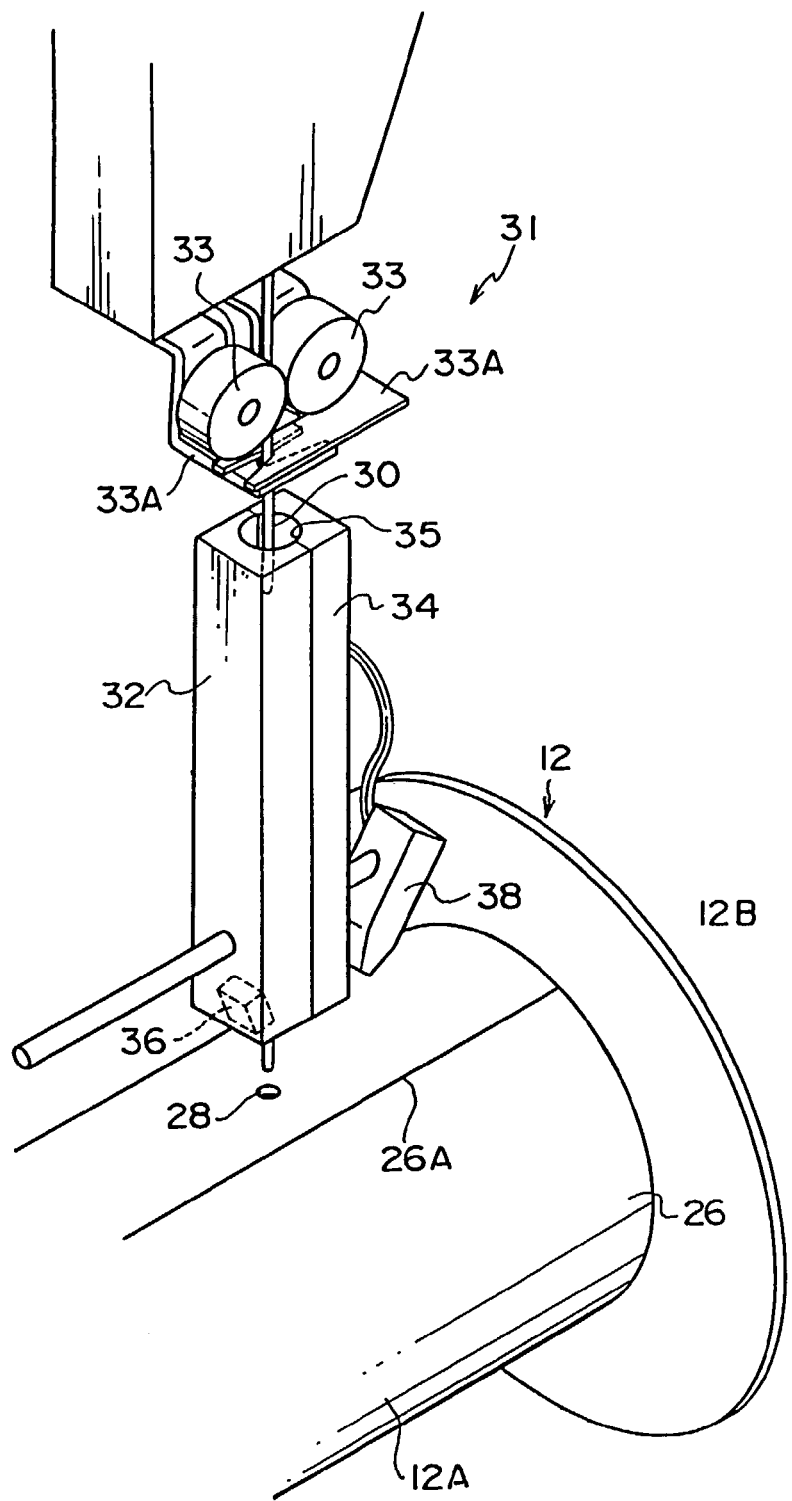
FIG. 2 is an enlarged perspective view showing an essential portion of the embodiment shown in FIG. 1.

As seen from FIG. 2, a cord winding portion (or core portion or drum) 12A of the spool 12 is constructed of a coated metal sheet 26, which has a seam (also called the "core edge") 26A formed in the axial direction of the spool 12. In the vicinity of the core edge 26A, there is formed a cord insertion hole 28.

This cord insertion hole 28 has a center position located at a distance L1 from the closer flange 12B and at a shorter distance L2 taken along the outer circumference from the core edge 26A (Refer to FIG. 1).

In the vicinity above the spool 12, there is disposed a cord insertion guide unit 31 for guiding the leading end of a cord (or insertion member) 30. This unit 31 can be moved back and forth by the not-shown drive device (e.g., an air cylinder) between a guide position, which is close to the spool 12 shown in FIG. 1, and a standby position which is separated therefrom in the depthwise direction of the drawing of FIG. 1.

On the upper side of the cord insertion guide unit 31 at the insertion position, there are disposed a pair of dispensing rollers 33. These dispensing rollers 33 are enabled to move up and down and toward and away from each other by the not-shown moving means.

The dispensing rollers 33 clamp the portion of the cord 30 near the leading end of the cord 30, and move downward in the clamping state to bring the cord leading end portion close to the cord insertion guide unit 31, and then rotate to let the cord leading end portion go into the cord insertion guide unit 31.

Near the respective dispensing rollers 33, there are disposed guide plates 33A, so that the cord 30 is inserted into the rhombic guide hole which is formed by the V-grooves of the two guide plates 33A overlapping each other.

The cord insertion guide unit 31 includes a pair of left and right guides 32 and 34. These two guides 32 and 34 are enabled by the not-shown drive means to move relatively in the direction (as indicated by arrow D of FIG. 1) toward each other and in the direction (as indicated by arrow E) away from each other. The two guides form a funnel-shaped guide hole 35 when they approach each other relatively.

On the inner side of the leading end of one guide, for example the guide 32, there is disposed a scanning reflection type photosensor (or coordinate detecting means) 36 which is electrically connected with the control device 24. On the outer side of the leading end of the other guide, for example the guide 34, there is disposed a color mark sensor (or auxiliary detecting means) 38 which is electrically connected with the control device 24.

The guides 32 and 34 and the color mark sensor 38 are enabled to move along a guide rod 40 in the axial directions of the spool 12 (i.e., in the directions of arrows E and F of FIG. 1) by a stepping motor 42 and a gear 44 (or moving means) which are mounted on the cord insertion guide unit 31. The stepping motor 42 is electrically connected with the control device 24 through a motor driver 46.

The reflection type photosensor 36 has a light emitting portion and a light receiving portion directed to a predetermined position on the extension of the cord 30 to be guided by the guide hole 35. By scanning the photosensor 36 in the axial directions of the spool 12, it is possible to detect the coordinates of two points (B1, B2) of intersections between the circumference of the cord insertion hole 28 and a predetermined straight line (or the straight line in the axial direction of the spool 12).

As shown in FIG. 3A, more specifically, the coordinates of the points B1 and B2 are detected by scanning the reflection type photosensor 36 together with the cord insertion guide unit 31 in the direction of arrow E (FIG. 3A) along a line C which is made by joining the points B1 and B2 of a semicircle below a center line S with respect to the cod insertion hole 28.

The operation of the present embodiment will be described hereinafter.

First of all, when the spool 12 is held/clamped by the spool holding arms 14 and 16, the cord insertion guide unit 31 approaches and abuts against the spool 12. The two guides 32 and 34 form the funnel-shaped guide hole 35, as has been previously described.

Next, the servomotor 20 is activated by a signal from the control device 24 to rotate the spool 12 in a predetermined direction, i.e., in the direction of arrow C of FIG. 1 in this embodiment. Simultaneously with this rotation, the core edge 26A of the spool 12 is detected by the color mark sensor 38 so that the spool 12 is stopped at the detected position (to determine a measurement reference position).

Next, on the basis of data stored in the control device 24, the servomotor 20 is turned again by a predetermined amount a to move the cord insertion hole 28 to the correcting scan starting coordinates generally below the reflection photosensor 36. At this time, the predetermined amount a is so set that the leading end portion of the cord insertion guide unit 31 may come to the semicircle below (or upstream of the rotation direction C) the center line S with respect to the cord insertion hole 28.

Next, on the basis of the stored data, the stepping motor 42 is driven to scan the reflection type photosensor 36 together with the cord insertion guide unit 31 in the direction of arrow E along the line C, as shown in FIG. 3A, to thereby detect the coordinates of the points B1 and B2, and is stopped at the point B2.

Where the coordinates of the points B1 and B2 cannot be detected due to variation or the like in the positional precision of the cord insertion hole 28, the take-up servomotor 20 is turned by a predetermined extent θ on the basis of the data stored in the control device 24, so that the cord insertion hole 28 is moved to the measurement reference position to detect the coordinates the points B1 and B2 again.

When the coordinates of the points B1 and B2 are then detected, the distance y between the points B1 and B2 is determined in the control device 24 from the coordinates of the points B1 and B2. On the other hand, the distance x between the straight line C and the center P of the cord insertion hole 28 is calculated by the following EQUATION, to determine the coordinates of the center P of the cord insertion hole 28:

$$X=\sqrt{\{r^2-(y/2)^2\}},$$

(wherein r designates the radius of the cord insertion hole 28).

Next, in order that the leading end center of the guide hole 35 may be opposed to the calculated coordinates of the center P of the cord insertion hole 28, the control device 24 drives and controls the stepping motor 42 to move the cord insertion guide unit 31 by a distance of y/2 in the direction of arrow F, and drives the take-up servomotor 20 to rotate the spool 12 so that the center P of the cord insertion hole 28 may move by the distance x in the direction of arrow G of FIG. 3B.

As a result, the leading end center of the guide hole 35 is aligned highly precisely to the center P of the cord insertion hole 28. After this, the cord 30 is clamped near its leading end portion by the paired dispensing rollers 33 at the upper standby position. Then, the dispensing rollers 33 are moved downward to bring the cord leading end close to the cord guide hole 35. Next, the dispensing rollers 33 are rotated to dispense the cord 30 to a predetermined extent and insert it into the cord insertion hole 28.

As the leading end portion of the cord 30 is inserted into the cord insertion hole 28, the two guides 32 and 34 leave each other to form the space for the cord 30 to pass through, and the cord insertion guide unit 31 then moves to a withdrawal position in the depth direction with respect to the paper surface in FIG. 1.

After this, the spool 12 is rotated to start the winding-up of the cord 30, and the paired dispensing rollers 33 move apart from each other to release the clamped state of the cord 30 until they return to the upper standby position.

Thus, in the present embodiment, the coordinates of the two circumferential points B1 and B2 on the straight line C in the cord insertion hole 28 are detected by the reflection type photosensor 36 and are operated by the control device 24 to determine the center coordinates of the cord insertion hole 28. As compared with the case employing the CCD camera, therefore, the center coordinates of the cord insertion hole 28 can be easily determined at a low cost.

Even if the center position (or coordinates) of the cord insertion hole 28 and the center of the guide hole 35 are misaligned at a distance less than half of the radius of the cord insertion hole 28, this misalignment can be corrected. A highly precise positioning can thus be carried out at a low cost. If the variation of the center coordinates of the cord insertion hole 28 is within one half of the hole diameter of 2r, a high speed positioning (within 2 seconds) and high precision (within 0.1 mm) can be realized at a low cost.

Further in the present embodiment, the core edge 26A of the spool 12 for providing the measurement reference position can be stably detected by the color mark sensor 38 without being affected by a painting flaw or the like, so that the positioning can be speeded up by moving the reflection type photosensor 36 from the measurement reference position to the correcting scan starting coordinates.

In the present device, where the coordinates of the points B1 and B2 of the cord insertion hole 28 could not be detected, the take-up servomotor 20 is rotated to a predetermined extent θ on the basis of the data stored in the control device 24, to thereby detect the coordinates of the points B1 and B2 again, so that the center of the cord insertion hole 28 can be reliably detected.

In the present embodiment, moreover, it is possible to automate the cord inserting operations which have been manually executed in the prior art.

It is needless to say that the present invention should not be limited to the embodiment thus far described but could be changed and modified in various manners within the scope of Claims. For example, the hole center detecting apparatus should not be limited to the cord insertion hole which is formed in the outer circumference portion of the spool but could be applied to the detection of a hole or the like formed in a flat face.

The coordinate detecting means should not be limited to the reflection type photosensor 36 and another sensor such as an ultrasonic sensor may be used. The auxiliary detecting means should not be limited to the color mark sensor 38 and another sensor such as a mechanical type sensor may be used.

The moving means should not be limited to the servo-motor 20 or the stepping motor 42 and by another moving means may be used.

<<Straightness Measuring Apparatus>>

In the following, one embodiment of a straightness measuring apparatus according to the present invention will be described with reference to FIGS. 4 to 10. First of all, however, a measurement plate constructing an essential portion of the present embodiment will be described with reference to FIGS. 4 and 5.

The straightness measuring apparatus 110 of the present embodiment includes a measurement plate 114 for placing a cord (or an object to be measured) 112 thereon. In the upper face of the measurement plate 114, there are formed three slits 116 which are parallel in the widthwise direction (or in the direction of arrow W). These slits 116 are formed to extend from the vicinity of one widthwise end 114A to the other widthwise end 114B continuously and further to a slope portion 114C. Above and below those slits 116, there are transparent type optical fiber sensors (or coordinate detecting means) 120, 122 and 124 disposed such that their respective light emitting portions and light receiving portions are opposed to each other. These optical fiber sensors 120, 122 and 124 are fixed on a moving arm 126.

Figure 4:
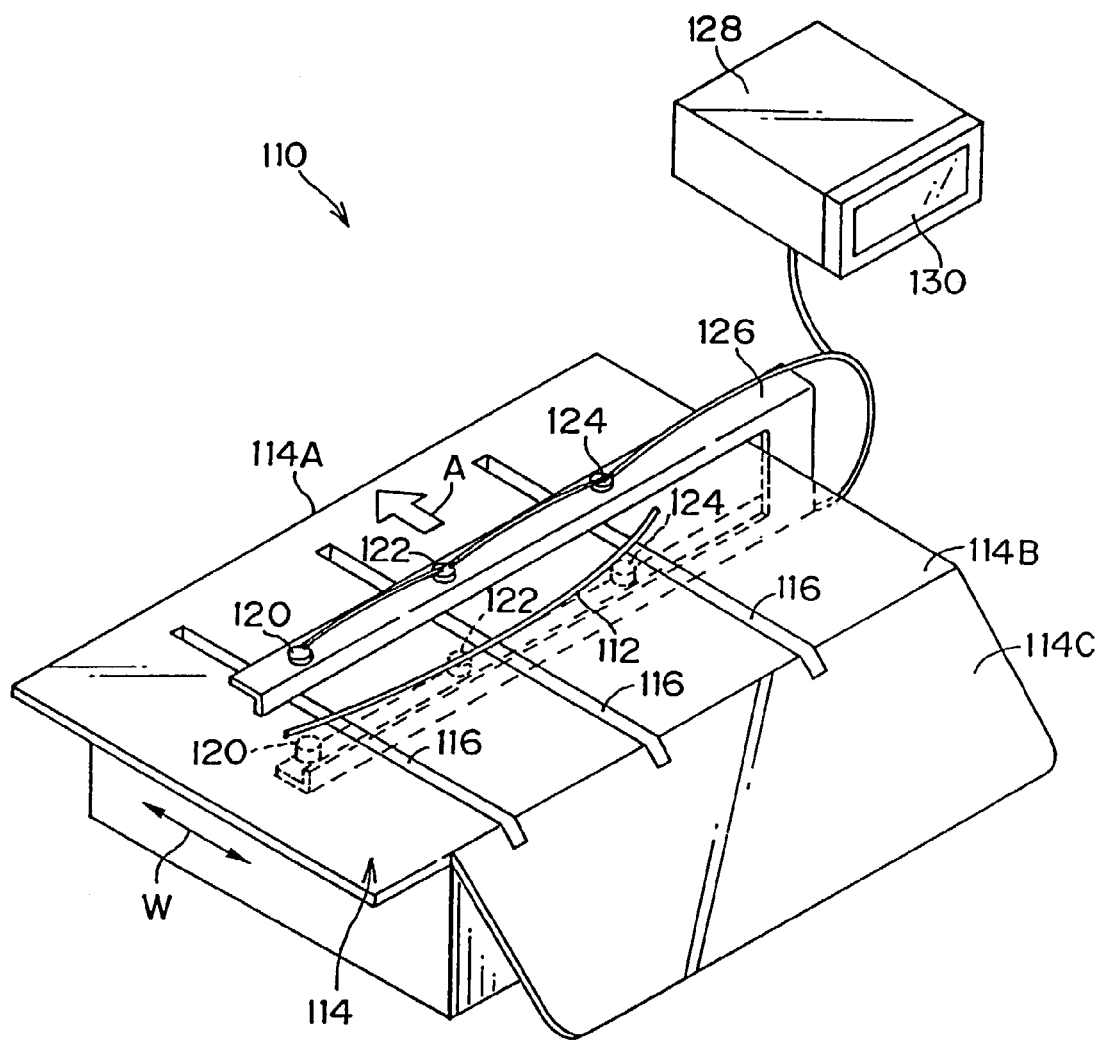
FIG. 4 is a perspective view showing a measurement plate forming an essential portion of one embodiment of a straightness measuring apparatus according to the present invention.
Figure 5:
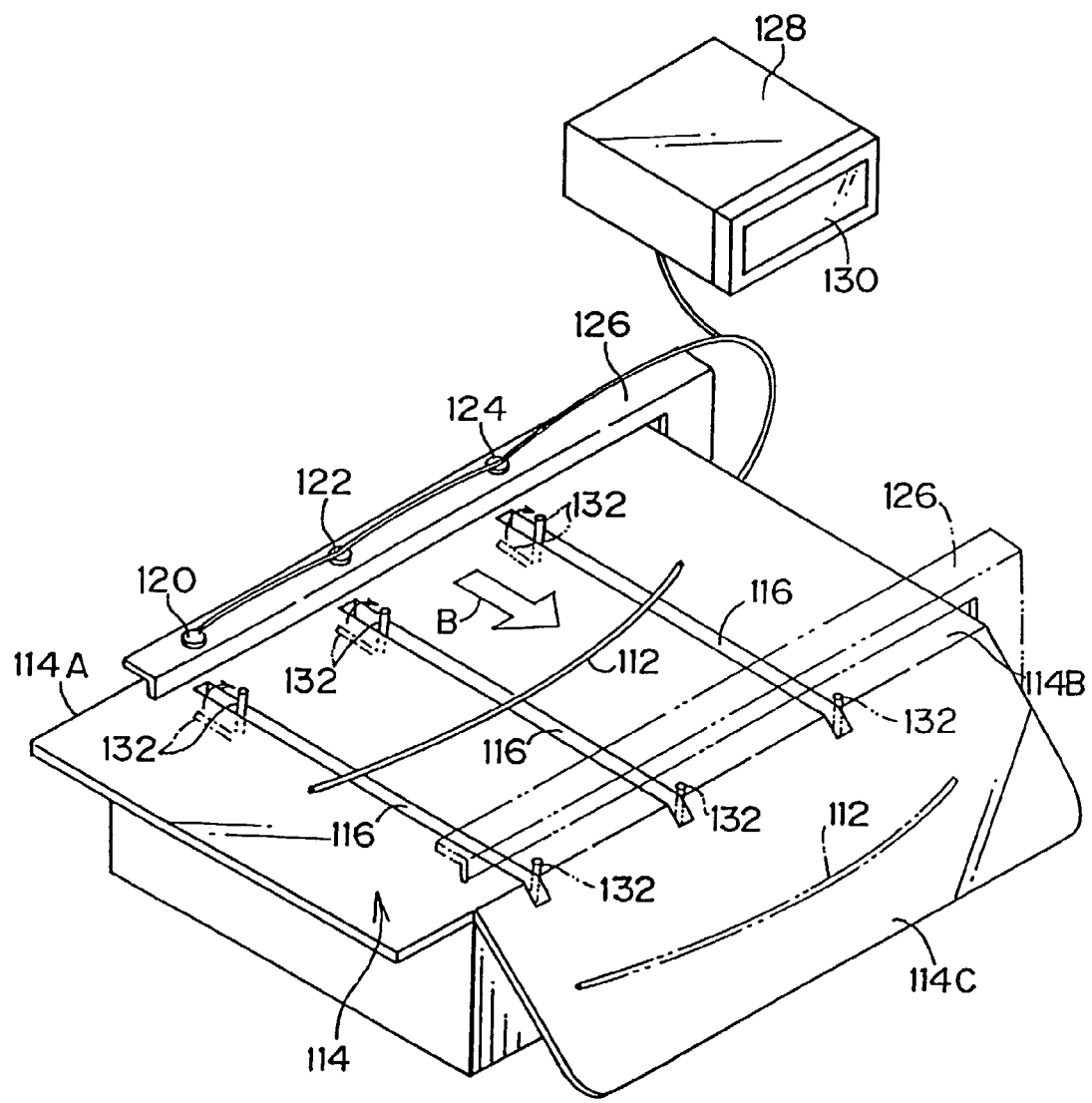
FIG. 5 is a perspective view showing the measurement plate shown in FIG. 4 with a moving arm being in a return position.

This moving arm 126 is enabled to move by drive means such as a motor to move between a measurement starting position on the side of the end portion 114B of the measurement plate 114, as indicated by double-dotted lines in FIG. 5, and a return position on the side of the end portion 114A, as indicated by solid lines in FIG. 5. As the moving arm 126 moves in the direction from the measurement starting position to the return position (or in the direction of arrow A of FIG. 4), the coordinates of three different points in the longitudinal direction of the cord 112 can be detected by the sensors 120, 122 and 124.

These sensors 120, 122 and 124 are electrically connected with a control device (or straightness computing means) including a computer. The control device 128 computes the straightness of the cord 112 from the curvature of a curve passing through the coordinates of the three points detected by the respective sensors 120, 122 and 124. The control device 128 is provided with a display (or display means) for displaying numerical values for the computed straightness of the cord 112.

Dispensing pins 132 are disposed respectively at the moving arm portions opposed to the slit 116, as shown in FIG. 5. These dispensing pins 132 are enabled by the (not-shown) drive means composed of air cylinders or the like to move between fall positions, at which they are hidden below the measurement plate 114, as indicated by double-dotted lines in FIG. 5, and rise positions at which their leading ends protrude over the measurement plate 114, as indicated by solid lines in FIG. 5.

When the moving arm 126 is at the return position (or at the solid-line position of FIG. 5), the dispensing pins 132 are moved from the fall positions to the rise positions. As the moving arm 126 moves in the direction of the measurement starting position (or in the direction of arrow B) indicated by the double-dotted lines, the cord 112 can be further dispensed to the slope portion 114C by the dispensing pins 132. The cord 112 thus dispensed, drops down along the slope portion 114C so that it is stored in the not-shown storage box.

Next, a straightness sampling device (simply called the "sampling device" hereinafter) for cutting the cord 112 to a predetermined sampling length and placing it on the measurement plate 114 will be described in detail with reference to FIGS. 6 to 8.

Figure 6:
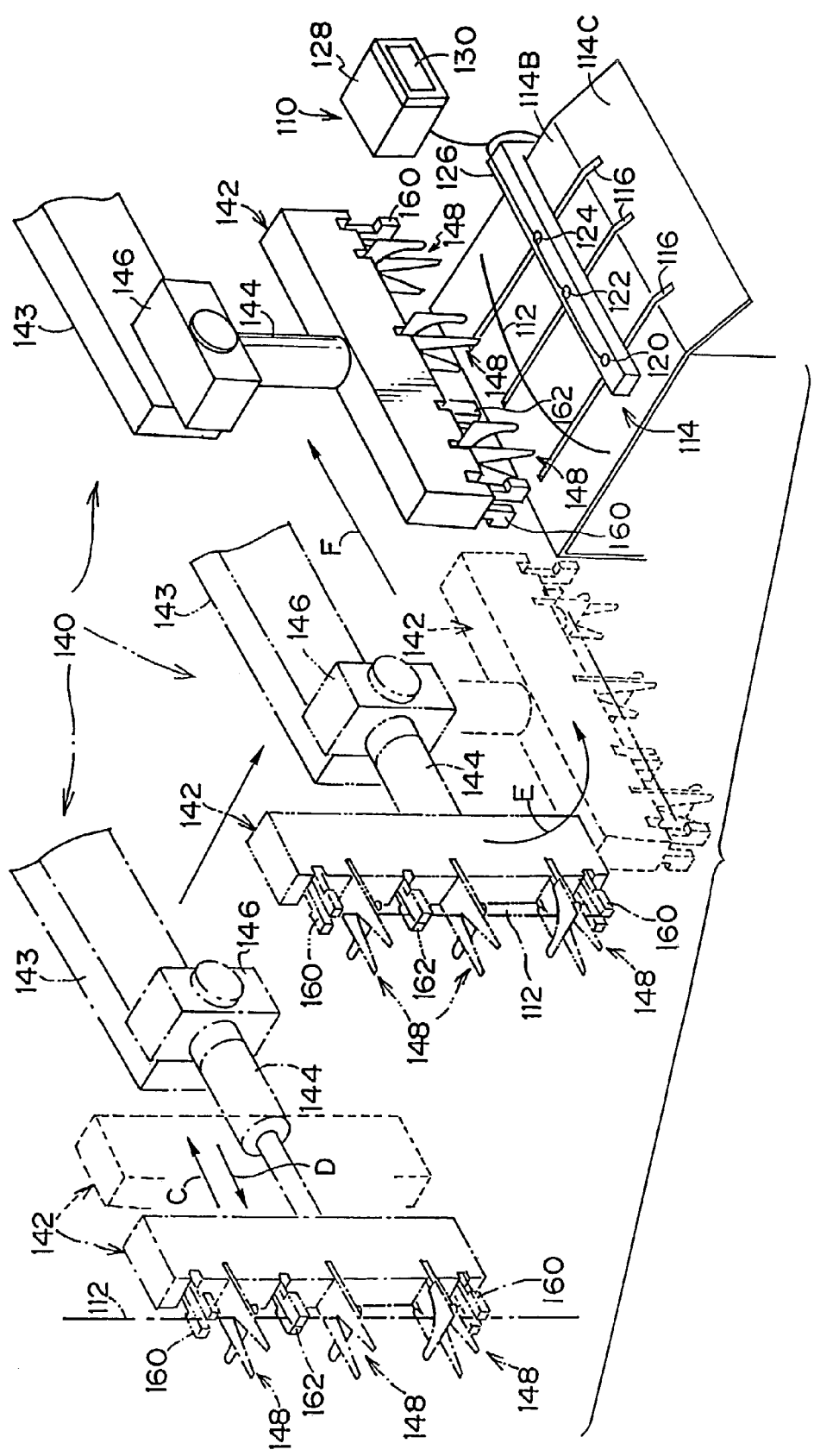
FIG. 6 is a perspective view showing a straightness sampling device forming another essential portion of the embodiment of the straightness measuring apparatus according to the present invention.

As shown in FIG. 6, the sampling device 140 of the present embodiment, at a sampling position indicated by single-dotted lines in FIG. 6: cuts a portion of the cord 112 wired in the cord take-up device or the like from the remaining portion; moves the cut portion to a placing position indicated by solid lines in FIG. 6, through a rotation position indicated by double-dotted lines in FIG. 6; and places the cord sample 112 on the measurement plate 114.

At the leading end portion of the sampling device 140, there is disposed a sampling unit 142. This sampling unit 142 is enabled to move back and forth in the cylinder axis directions (or in the directions of arrows C and D) by an air cylinder 144 which is mounted on an arm 143.

The sampling unit 142 is enabled to rotate with respect to the arm 143 by a rotor 146. More specifically, the sampling unit 142 can rotate from a vertical position, as indicated by double-dotted lines of FIG. 6, to a horizontal position (or in a state in parallel with the upper face of the measurement plate 114), in which it is inclined downward by 90 degrees (or in the direction of arrow E) and indicated by broken lines, and vice versa.

The arm 143 is enabled by the not-shown drive means to move in a placing direction (or in the direction of arrow F of FIG. 6) from the position for a tilting (or rotating) motion, and vice versa.

The sampling unit 142 is provided with three guide units 148 in its longitudinal direction.

Figure 7:
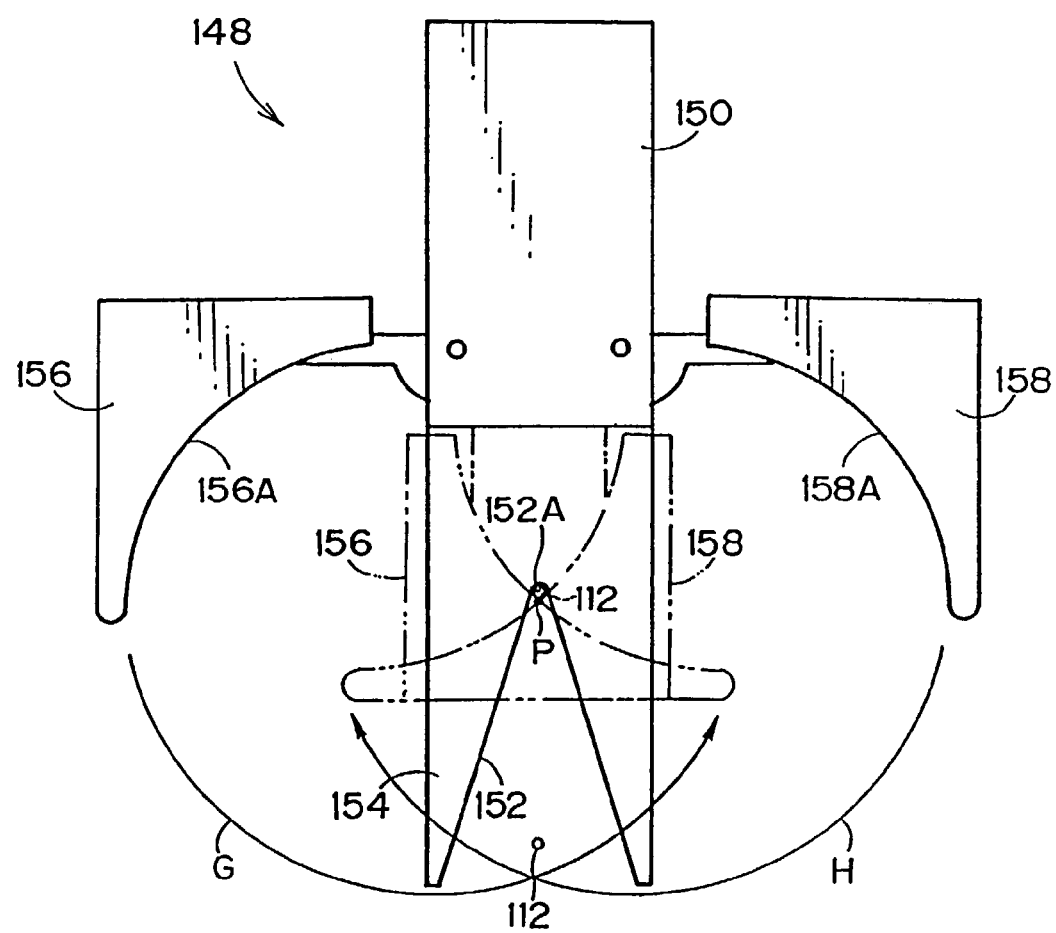
FIG. 7 is a top plan view showing a guide unit of the sampling device shown in FIG. 6.

To the leading end side of a unit base 150 of the guide unit 148, as shown in FIG. 7, there is attached a stationary guide 154 which has a V-shaped recess 152. On the two sides of the stationary guide 154, a pair of left and right moving guides 156 and 158 are rotatably mounted on the unit base 150. The two guides 156 and 158 are respectively enabled by drive means composed of air cylinders or the, like to move between standby positions, at which they are spaced apart, as indicated by solid lines in FIG. 7, and guide positions at which they partially overlap each other, as indicated by double-dotted lines.

The opposed guide faces 156A and 158A of the moving guides 156 and 158 have a substantially quarter arc shape. While the moving guides 156 and 158 are moving in the directions from the standby positions to the guide positions (or in the directions of arrows G and H), for example, the cord 112 in the vicinity of the opening of the recess 152 of the stationary guide 154 can be moved to the vicinity of a bottom portion 152A of the recess 152. When the moving guides 156 and 158 come to the guide positions, a line of intersection P, between the guide face 156A and the guide face 158A is placed in the vicinity of a position opposing the bottom portion 152A of the recess 152 in the stationary guide 154 so that the cord 112 can be positioned in the direction perpendicular to the cord axis. The cord 112 thus positioned is restricted relatively loosely so that it can slidably move in the cord axis direction and slidably rotate on the axis to some extent.

Figure 8:
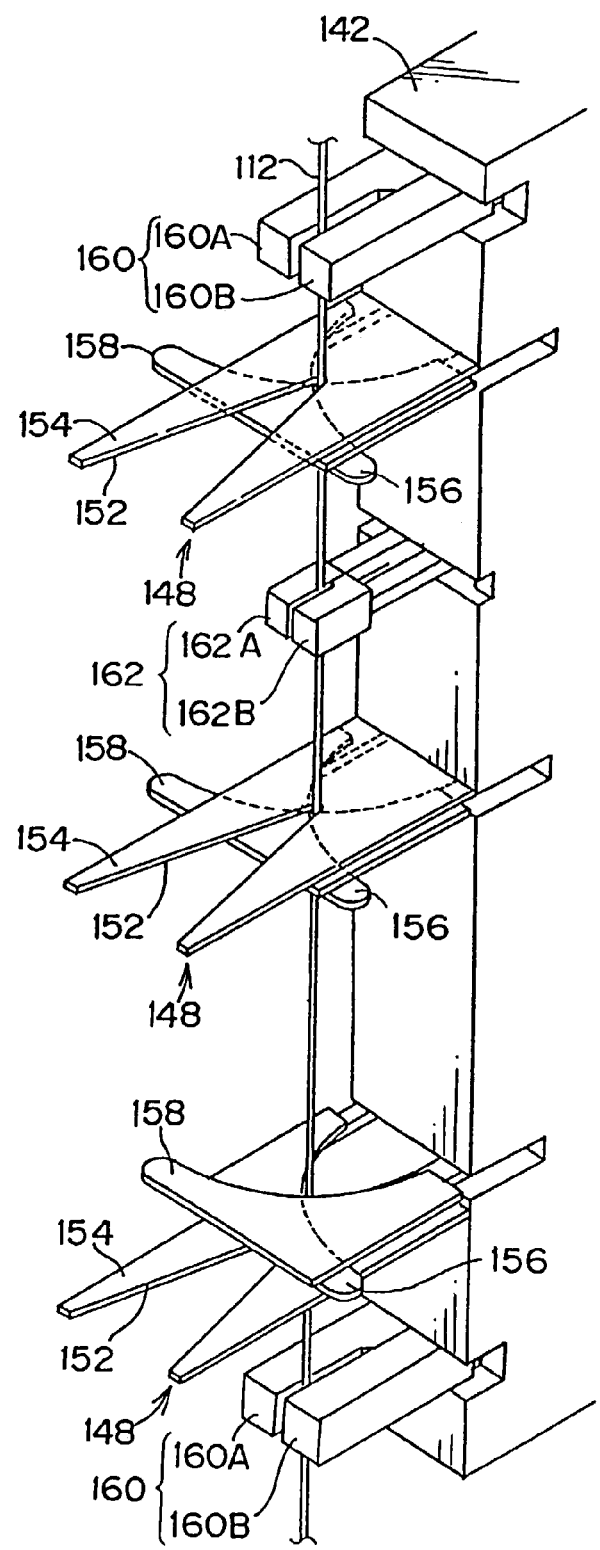
FIG. 8 is an enlarged perspective view showing an essential portion of the sampling device shown in FIG. 6.

At the two longitudinal ends of the sampling unit 142, as shown in FIG. 8, there are respectively disposed thermal shearing chucks 160. Thermal shearing refers to the cord being cut as a result of being melted due to the high temperature of the chucks. Each of these thermal shearing chucks 160 is provided such that they can be opened and include thermal shearing portions 160A and 160B for pinching the cord 112 to thereby thermally shear it.

Between the upper guide unit 148 and the central guide unit 148, as shown in FIG. 8, there is disposed a chuck 162. This chuck 162 includes holding portions 162A and 162B for clamping the cord 112 positioned by the guide unit 148, and is provided such that the chuck can be opened. As the sampling unit 142 moves to the placing position, as shown by the solid lines in FIG. 6, the chuck 162 is opened to release the clamped state of the cord 112. At the same time, the moving guides 156 and 158 move in the directions from the guide positions to the standby positions (i.e., backwards from the direction of arrow G and the direction of arrow H) so that the cord 112 is entirely released from the hold and drops onto the measurement plate 114.

Here the operation of the present embodiment will be described.

Where the sampling device 140 is positioned at the sampling position indicated by the single-dotted lines in FIG. 6, the moving guides 156 and 158 of each guide unit 148 move from the standby positions to the guide positions so that the cord 112 is positioned. Next, the positioned cord 112 is clamped by the chuck 162 and is cut to the predetermined length by the soldering chucks 160.

Next, at the rotation position indicated by the double-dotted lines in FIG. 6, the rotor 146 tilts the air cylinder 144 (and the sampling device 140) into the direction of arrow E so that the sampling device 140 is parallel to the measurement plate 114.

Next, the arm 143 is moved by the (not-shown) drive means from the rotation position to the placing position, as shown by the solid lines in FIG. 6. At this moved placing position, the chuck 162 is opened to release the clamped state of the cord 112. At the same time, the moving guides 156 and 158 are moved in the direction from the guide positions to the standby positions so that the cord (sample)of a predetermined length which is thus completely released, drops onto the measurement plate 114 of the straightness measuring apparatus 110.

When the cord 112 is placed on the measurement plate 114, the moving arm 126 moves in the direction from the measurement starting position to the return position (or in the direction of arrow A of FIG. 4). At this time, the coordinates of the three different points in the longitudinal direction of the cord 112 are detected by the sensors 120, 122 and 124.

The control device 128 determines the curvatures of the curves passing through the coordinates of the three points, as detected by the sensors 120, 122 and 124, to compute the parameters relating the-straightness of the cord 112, from computing equations (1) to (6) of FIG. 10, as will be specified in the following.

Given that the coordinates of three points A, B and C are expressed by detected coordinates A=(Ax, Ay), detected coordinates B=(Bx, By) and detected coordinates C=(Cx, Cy), a straight line which passes at a right angle through the center point of a straight line AB and a straight line which passes at a right angle through the center point of a straight line BC are derived from equations (1) and (2), respectively.

The center coordinates (X, Y) of a curve passing through the detected coordinates A, B and C are the intersection of the aforementioned two straight lines and are determined from equations (3) and (4).

The radius of curvature $\rho$ is determined from equation (5).

The straightness (or the curvature) H per cord length L is determined from equation (6).

The control device 128 displays the computed straightness H of the cord 112 in numerical values on the display 130.

In the present embodiment, as has been described above, the straightness of the cord 112 is computed by detecting the coordinates of the three different points in the longitudinal direction of the cord 112 with the transparent type optical fiber sensors 120, 122 and 124 and by determining the curvature of the curve passing through the coordinates of the three detected points, and the result is displayed on the display 130. Therefore, it is possible to quantitatively confirm the straightness of the cord 112 quickly and automatically. This confirmation eliminates the variation which might otherwise be caused by the manual measurements, so that the productivity can be drastically improved. It is therefore, possible to provide a steel cord for reinforcing a rubber part, or a wire for another application, in a timely manner and at a low cost.

In the present embodiment, the coordinates of the three different points in the longitudinal direction of the cord 112 are detected by the transparent type optical fiber sensors 120, 122 and 124. Even where the cord 112 has undulations in the direction toward the transparent type optical fiber sensors 120, 122 and 124, that is, even where the cord 112 comes up from off the measurement plate 114, therefore, the straightness can be measured more precisely than with the apparatus employing the reflection type optical fiber sensors.

Figure 9:
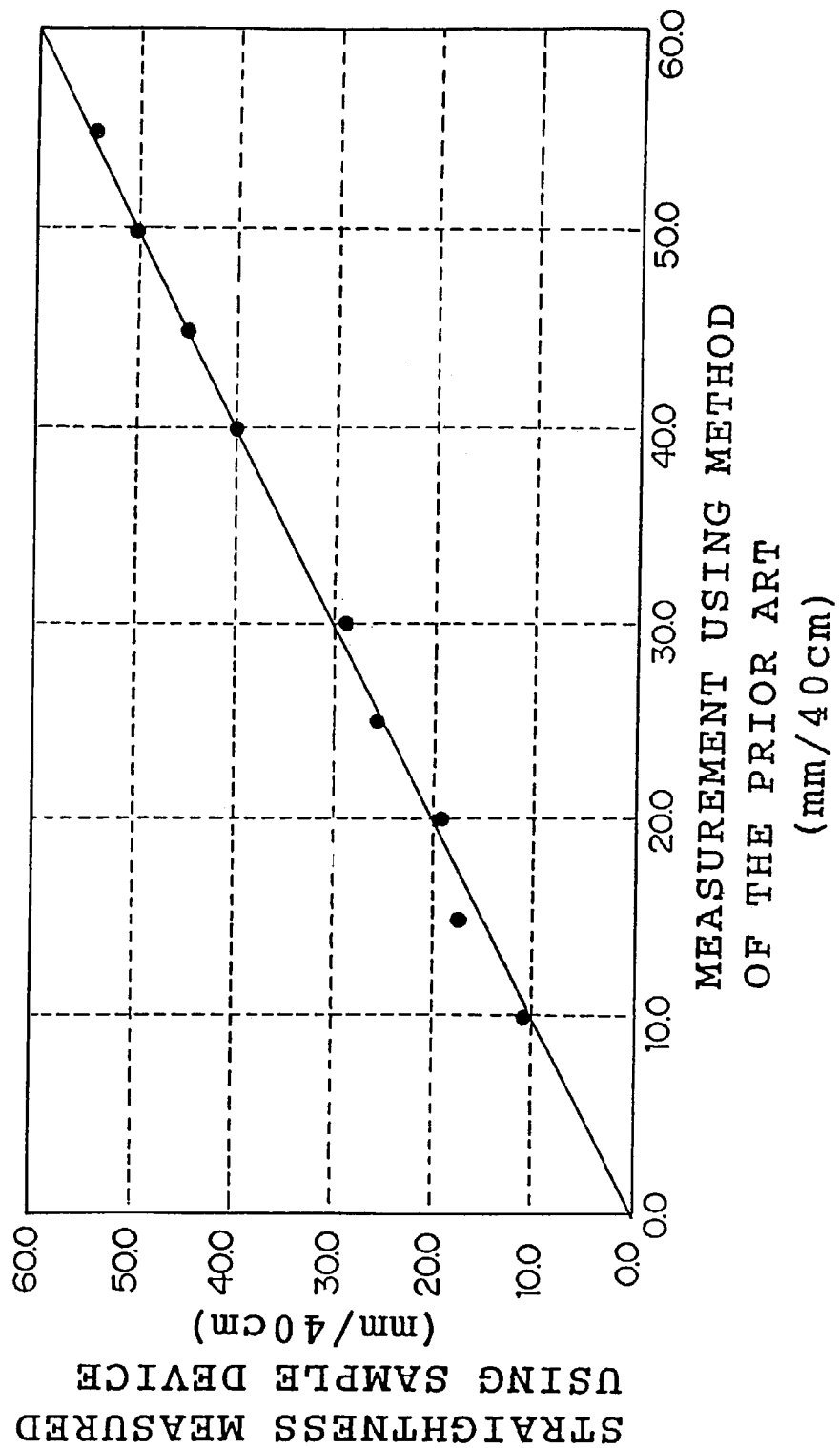
FIG. 9 is a diagram for comparing and evaluating the values of the straightness of the cord, as measured by the sampling device of FIG. 6, with the values of the visual measurement of the prior art.

In FIG. 9 the results of comparing the values of the straightness of the cord 112 (having a length of 40 cm), as measured by the apparatus of the present embodiment, with the visually measured values are shown. As could be understood from FIG. 9, the measured values of the straightness of the present embodiment and the visually measured values are substantially equal.

It is needless to say that the present invention should not be limited to the aforementioned embodiment but could be changed and modified in various manners within the scope of Claim. For example, the coordinate detecting means to be employed could be another sensor such as a reflection type optical fiber sensor, an ultrasonic sensor or a mechanical type sensor. Also, the detecting precision can be better improved by scanning the transparent type optical fiber sensors 120, 122 and 124 several times to detect the coordinates of the three points for each scan. Further, the construction may be modified such that the coordinates of four or more different points in the longitudinal direction of an object to be measured are detected by the coordinate detecting means.

In place of the display 130, there could be employed another display means such as a digital meter. In order that the cord 112 may be reliably held on the measurement plate 114, this measurement plate 114 could be provided with cord holding means such as an electromagnet or a permanent magnet.

<<Residual Torsion Measuring Apparatus>>

One embodiment of the residual torsion measuring apparatus according to the present invention will be described in the following with reference to FIGS. 11 to 16. This residual torsion measuring apparatus basically includes: a bending unit for bending the end portion of a cord at a specified angle; and a unit for measuring and displaying the residual torsion of the bent cord.

Figure 11:
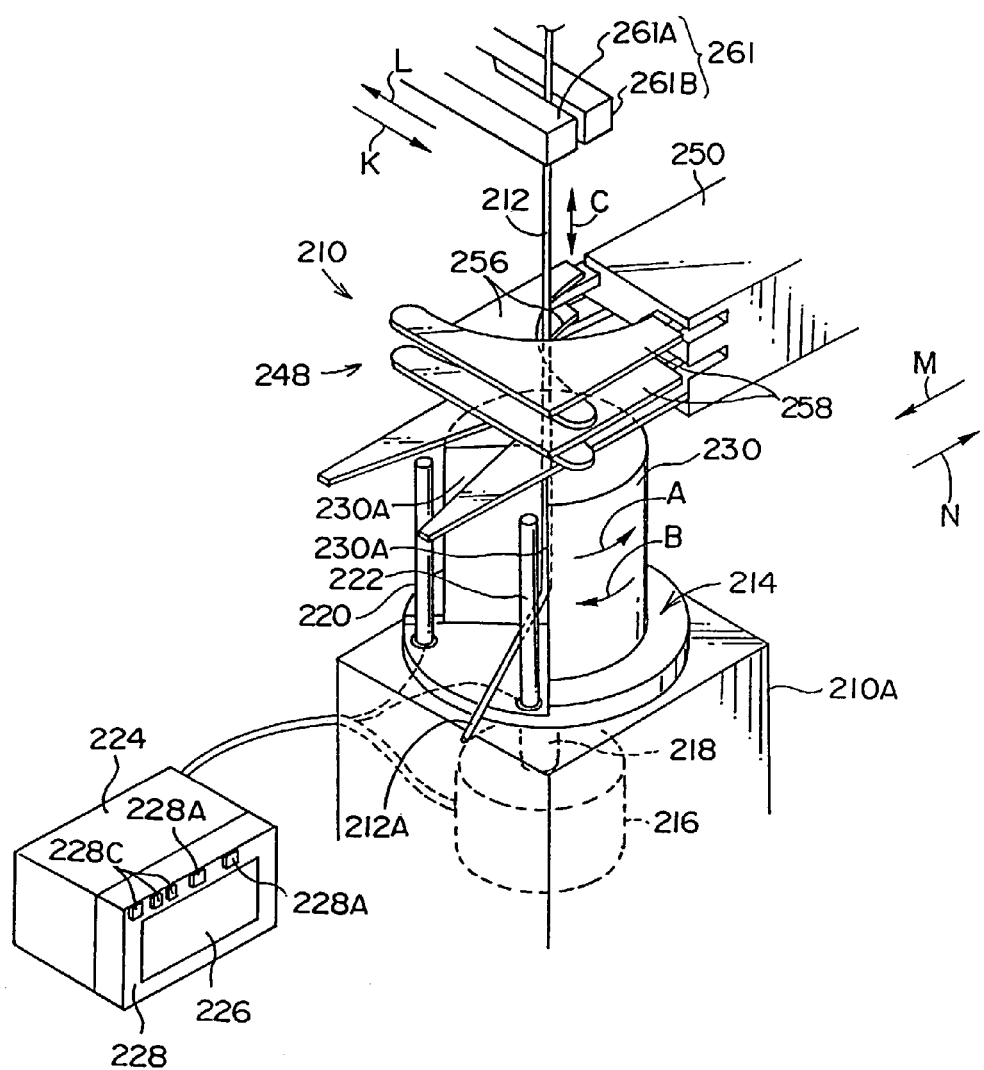
FIG. 11 is a perspective view showing one embodiment of a residual torsion measuring apparatus according to the present invention.

As shown in FIG. 11, a base 210A of the residual torsion measuring apparatus 210 of the present embodiment is enabled by the (not-shown) drive device to move in the downward direction of a cord 212 or an object to be measured (or in the direction of arrow M of FIG. 11) and in the direction away from the cord 212 (or in the direction of arrow N of FIG. 11). A cord lower end portion 212A is bent at a predetermined angle θ, and the cord portion above a predetermined distance (e.g., 5 m) from the cord lower end is so held by the (not-shown) holding means that the cord 212 may not rotate on the axis.

Above the base 210A, there is disposed a rotor (or drive means) 214. This rotor 214 is enabled to rotate on a spindle 218 in the directions of arrows A and B by a motor 216 which is disposed in the base 210A.

At the flanged portion of the upper face of the rotor 214, there are disposed two rod-shaped electrodes 220 and 222 which are extended at a predetermined spacing and in parallel with the axial direction of the spindle 218. These electrodes 220 and 222 and the motor 216 are electrically connected with a control device (or operation control means) 224 composed of a computer. The control device 224 is provided with an operation portion 228 having a display (or display means) 226. In the operation portion 228, there are disposed switches 228A, 228B and 228C according to the kind or test standards of the cord 212. When the S-shaped switch 228A is pushed, for example, the clockwise rotation is indicated by "+", and the counter-clockwise rotation is indicated by "−". When the Z-shaped switch 228B is pushed, the counter-clockwise rotation is indicated by "+", and the clockwise rotation is indicated by "−". By operating the switch 228C, the rotating speed of the rotor 214 can be changed according to the diameter, material and so on of the cord 212.

On the upper face of the rotor 214, there is disposed a cover 230. This cover 230 is provided with wall portions 230A and 230B which extend from the vicinities of the electrodes 220 and 222 to the rotating center of the rotor 214, so that the end portion 212A of the cord 212 may reliably contact with the electrodes 220 and 222 while being prevented from coming out of the electrodes 220 and 222.

The diameter, the material and so on of the cord 212 are inputted from the operation portion 228, and the control device 224 changes the rotating speed of the motor 216 accordingly.

Above the rotor 214, there is disposed a guide unit (or positioning means) 248 for preventing the cord 212 from moving perpendicularly to the axial direction (or the direction of arrow C). This guide unit 248 is enabled by the (not-shown) drive means to move integrally with the base 210A in the direction of arrow M and in the direction of arrow N of FIG. 11, thus moving between the positioning position shown in FIG. 11 and the standby position which is spaced apart from the cord 212.

Figure 12:
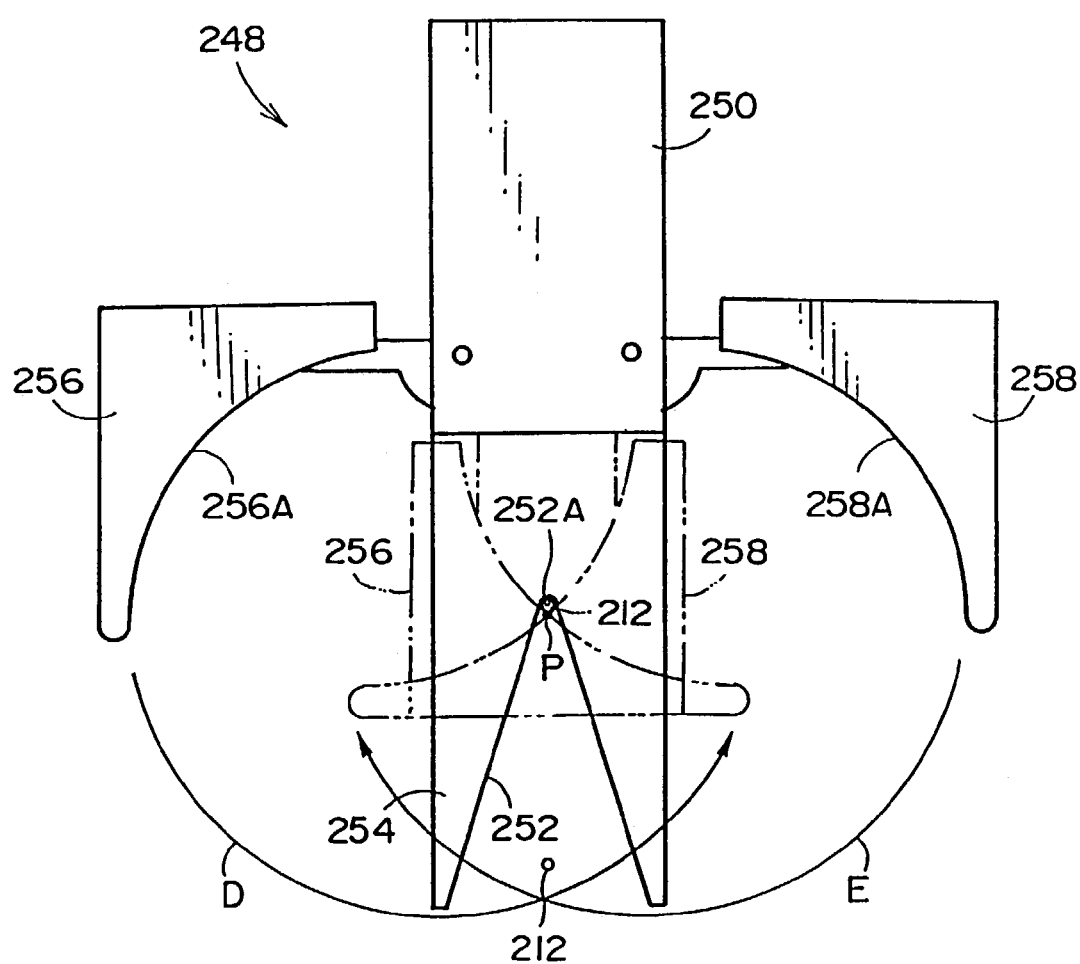
FIG. 12 is a top plan view showing a guide unit of the embodiment shown in FIG. 11.

To the leading end side of a unit base 250 of the guide unit 248, as shown in FIG. 12, there is attached a stationary guide 254 which has a V-shaped recess 252. Two of each pair of left and right moving guides 256 and 258 are aligned above and below the two sides of the stationary guide 254. The two guides 256 and 258 are rotatably attached to the unit base 250 and are respectively enabled by drive means such as air cylinders or the like to move between standby positions, at which they are spaced apart, as indicated by solid lines in FIG. 12, and guide positions at which they partially overlap each other, as indicated by double-dotted lines.

The opposed guide faces 256A and 258A of the moving guides 256 and 258 have an approximately quarter arc shape. While the moving guides 256 and 258 are moving in the directions from the standby positions to the guide positions (or in the directions of arrows D and E), for example, the cord 212 in the vicinity of the opening of the recess 252 of the stationary guide 254 can be moved to the vicinity of a bottom portion 252A of the recess 252. When the moving guides 256 and 258 come to the guide positions, a line of intersection P between the guide face 256A and the guide face 258A is positioned in a vicinity of a position which opposes to the bottom portion 252A of the recess 252 in the stationary guide 254 so that the cord 212 can be positioned in the direction perpendicular to the cord axis. The cord 212 thus positioned is restricted relatively loosely so that it can slidably move in the cord axis direction and slidably rotate on the axis to some extent.

Figure 14:
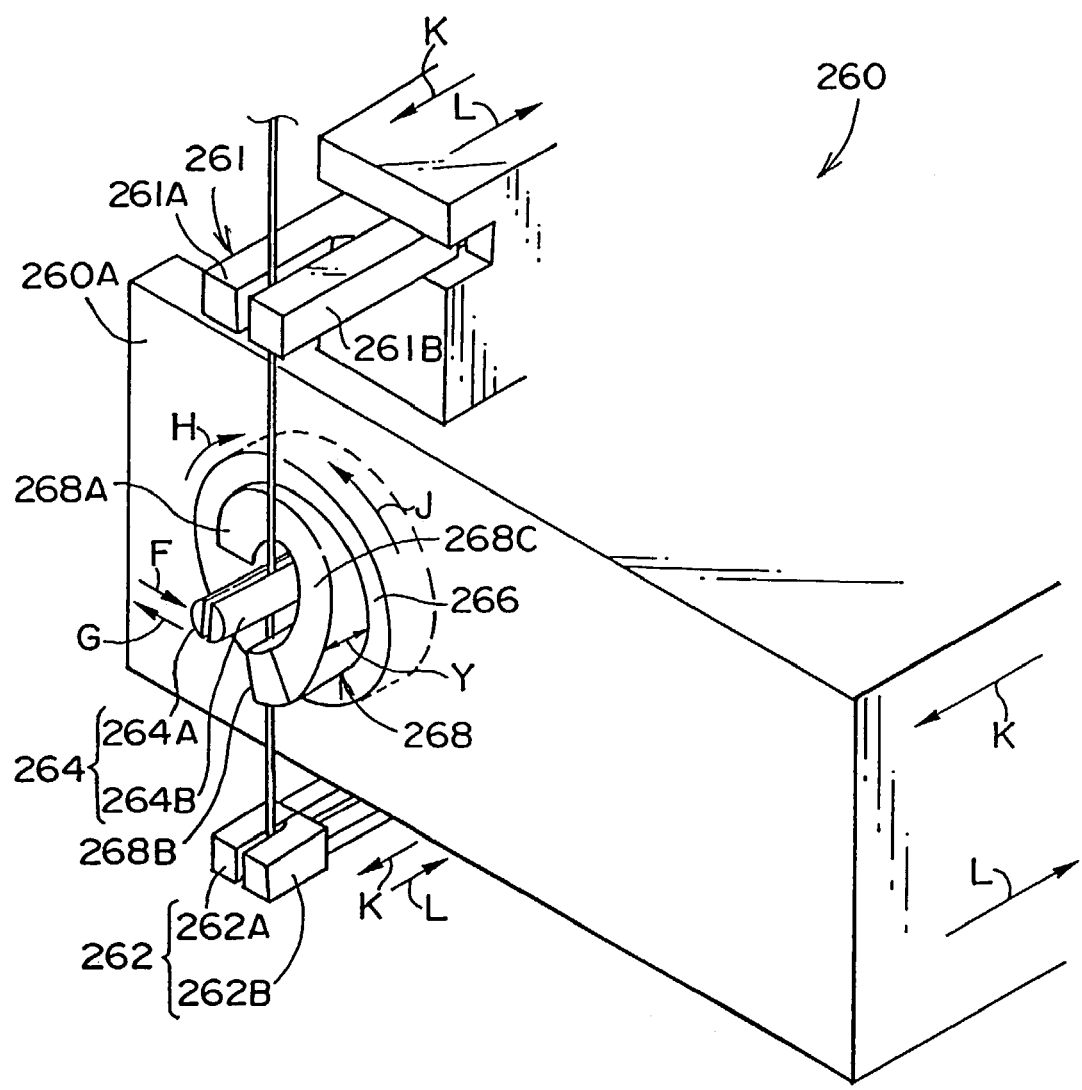
FIG. 14 is a perspective view of a bending unit of the embodiment shown in FIG. 11.

With reference to FIG. 14, FIG. 15A and FIG. 15B, here will be described a bending unit (or bending means) for cutting the cord 212, wired onto a cord take-up device, at its one portion and for bending its end portion 212A at a specified angle.

As shown in FIG. 14, the base portion 260A of a bending unit 260 of the present embodiment is enabled by the (not-shown) drive means to move in the direction toward the cord 212(or in the direction of arrow K of FIG. 14) and in the direction away from the cord 212(or in the direction of arrow L of FIG. 14). Above the base portion 260A, on the other hand, there is disposed a chuck 261. This chuck 261 is enabled by the (not-shown) drive means to move in the direction (or in the direction of arrow K of FIG. 14) toward the cord 212 and in the direction (or in the direction of arrow L of FIG. 14) away from the chuck 212. On the other hand, the chuck 261 has holding portions 261A and 261B opened/closed by the (not-shown) drive means so that they can clamp the cord 212, as shown in FIG. 14.

Below the base portion 260A, on the other hand, there is disposed a thermal shearing chuck 262. This thermal shearing chuck 262 is enabled by the (not-shown) drive means to move in the direction toward the cord 212 (or in the direction of arrow K of FIG. 14) and in the direction away from the cord 212(or in the direction of arrow L of FIG. 14). Here, the thermal shearing chuck 262 has thermal shearing portions 262A and 262B opened/closed by the (not-shown) drive means so that they can clamp and thermally shear the cord 212, as shown in FIG. 14.

On the side face of the base portion 260A, on the other hand, there is disposed a guide chuck 264. This guide chuck 264 is shaped by dividing a column longitudinally so that its holding portion 264A and 264B may receive the cord 212 in between as the bending unit 260 is brought close to the cord 212. On the other hand, one holding portion 264A is enabled by the (not-shown) drive means to move in the directions toward and away from the other holding portion 264B(or in the directions of arrows F and G). When the bending unit 260 comes close to the cord 212 to take a bending position, as shown in FIG. 14, the holding portion 264A moves toward the holding portion 262B to clamp the cord 212.

On the side face of the base portion 260A and around the outer circumference of the guide chuck 264, on the other hand, there is disposed a rotor 266, which is enabled to rotate in the directions of arrows H and J of FIG. 14 by a (not-shown) motor which is disposed as the drive means in the base portion 260A.

On the rotor 214, there is formed cam 268 having a variable rotation angle, and an arcuate shape when viewed in the direction of the rotating axis of the rotor 266. Also, the cam 268 has a height Y (or a protrusion in the direction of the rotating axis) which increases gradually in the rotating direction from one end portion 268A to the other end portion 268B thereby forming a slope face 268C between the two end portions.

Accordingly, as the rotor 266 is rotated by a predetermined angle in the direction of arrow H with the cord 212 being clamped between the chuck 261 and the guide chuck 264, as shown in FIG. 15A, the end portion 268B of the cam 268 disposed on the rotor 266 abuts against the end portion 212A of the cord 212 to push and bend the end portion 212A of the cord 212 in the rotation direction (or in the direction of arrow H). Here, the bending angle of the end portion 212A of the cord 212 can be changed by the rotation angle of the rotor 266. When the end portion 212A of the cord 212 is bent by a predetermined angle θ (e.g., θ=90 degrees±30 degrees), as shown in FIG. 15B, the rotor 266 rotates (backward) in the direction of arrow J. At this time, the holding portion 264A of the guide chuck 264 moves in the direction of arrow F of FIG. 14 to release the clamped state of the cord 212. At the same time, the cam 268 goes from the side of its end portion 268A into the space between a straight portion 212B of the cord 212 and the rotor 266 to push the cord 212 out of the guide chuck 264.

Here the operation of the present embodiment will be described.

First of all, the chuck 261 of the bending unit 260 moves in the direction of arrow K of FIG. 14 to clamp the cord 212. Next, the base portion 260A of the bending unit 260 moves in the direction of arrow K of FIG. 14. After this, the holding portion 264A of the guide chuck 264 moves in the direction of arrow F of FIG. 14 to clamp the cord 212. Next, the thermal shearing chuck 262 moves in the direction of arrow K of FIG. 14 to clamp and thermally shear the cord 212. After this, the thermal shearing portions 262A and 262B of thermal shearing chuck 262 separate from each other and move in the direction of arrow L of FIG. 14 away from the cord 212.

Next, with the cord 212 being clamped by the chuck 261 and the guide chuck 264, as shown in FIG. 15A and FIG. 15B, the rotor 266 rotates by a predetermined angle in the direction of arrow H to bend the end portion 212A of the cord 212 to a predetermined angle θ.

Next, the holding portion 264A of the guide chuck 264 moves in the direction of arrow G of FIG. 14 to release the clamped state of the cord 212. At the same time, the rotor 266 rotates (backward) in the direction of arrow J, and the cam 268 goes from the side of the end portion 268A into the space between the straight portion 212B of the cord 212 and the rotor 266 to push the cord 212 out of the guide chuck 264. After this, the base portion 260A of the bending unit 260 moves away from the cord 212 in the direction of arrow L of FIG. 14.

Next, the residual torsion measuring apparatus 210 moves, for example, in the direction perpendicular to the moving direction of the chuck 261 (or in the direction of arrow M of FIG. 11), toward the cord 212 clamped by the chuck 261. After this, the moving guides 256 and 258 of the guide unit 248 move from the standby position to the guide position to position the cord 212.

As a result, the end portion 212A of the cord 212 is inserted into the space between the two electrodes 220 and 222, as shown in FIG. 11.

Figure 13A:
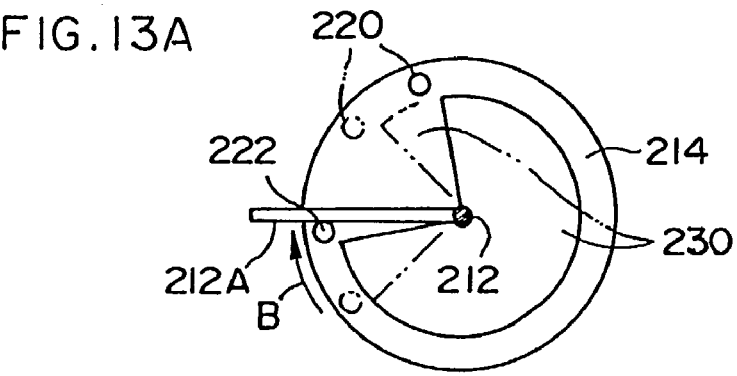
FIGS. 13A to 13D are diagrams showing the respective stages of the operation in the embodiment shown in FIG. 11.

Next, the rotor 214 is rotated in the direction of arrow B from the position indicated by the double-dotted lines, as shown in FIG. 13A, to bring one electrode 222 to abut against the end portion 212A of the cord 212. When the end portion 212A of the cord 212 abuts against the electrode 222, an electric signal is inputted to the control device 224 so that the control device 224 stops the rotation of the rotor 214 and stores a detection angle α1. After this, the holding portions 261A and 261B of the chuck 261 shown in FIG. 11 separate from each other, and move in the direction of arrow L of FIG. 11 to leave the cord 212.

Figure 13B:
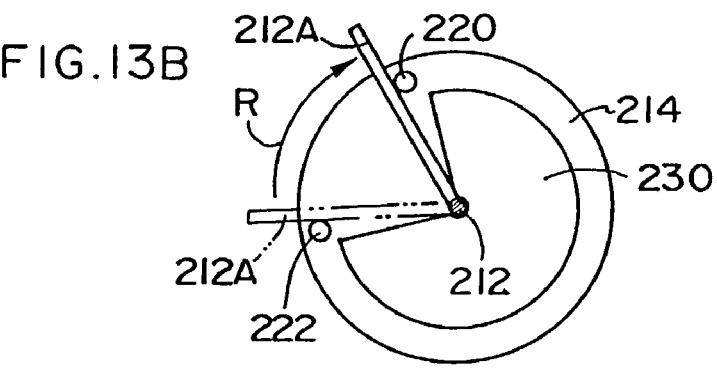

As a result, the residual torsion of the cord 212 turns the end portion 212A of the cord 212 in the direction of arrow R from the position indicated by double-dotted lines, as shown in FIG. 13B, to abut against the other electrode 220.

Figure 13C:
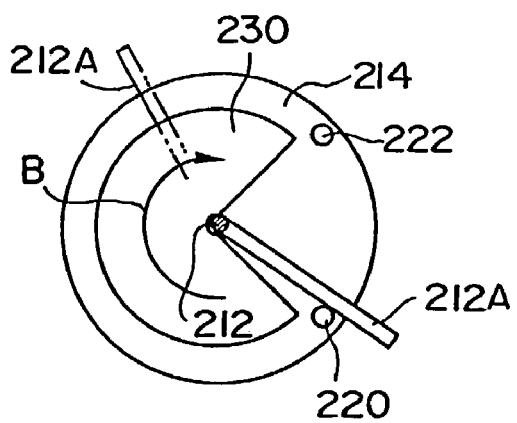
Figure 13D:
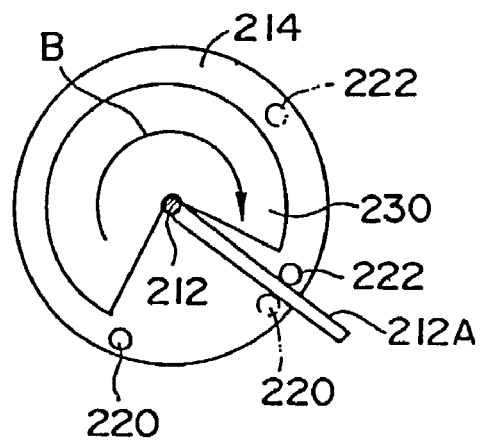

Next, the control device 224 rotates the rotor 214 in the direction of arrow B. Before the rotation angle of the rotor 214 reaches a predetermined value, as shown in FIG. 13C, the residual torsion of the cord 212 holds the end portion 212A of the cord 212 to abut against the electrode 220.

As the rotor 214 further rotates, the end portion 212A of the cord 212 leaves the electrode 220 and once again abuts against the electrode 222. The electric signal at this time is inputted to the control device 224 so that the control device 224 stops the rotation of the rotor 214 and stores a detection angle α2. At the same time, the control device 224 computes the residual torsion of the cord 212 from the difference between the detection angle α1 and the detection angle α2 and displays the computed residual torsion in the display 226 of the operation portion 228.

Thus, the residual torsion measuring apparatus 210 of the present embodiment can measure the residual torsion more precisely than when measured by an inspector and can improve the productivity. Further, by combining the apparatus 210 with other automated devices, moreover, the productivity can be enhanced to provide a steel cord for reinforcing a rubber part or a wire for another application at a low cost.

Also, in the present embodiment, by employing the electrodes 220 and 222 and the rotor 214, the residual torsion, which when manually measured had a precision of a quarter to a half rotation, can be measured more precisely than the measurement by the inspector since the residual torsion of the cord 212 is measured using the rotation angle of the rotor 214.

Further, in the present embodiment, the two electrodes 220 and 222 disposed across the end portion 212A of the cord 212 are employed to compute the residual torsion from the rotation angle α1 of the rotor 214 at the instant when the end portion 212A of the cord 212 contacts with the electrode 222 and the rotation angle α2 of the rotor 214 at the instant when the end portion 212A of the cord 212 contact with the electrode 222. When the residual torsion is computed from the rotation angle α1 of the rotor 214 at the instant when the end portion 212A of the cord 212 contacts with the electrode 222, chattering between the electrodes and the cord has less effect than when residual torsion is computed from the rotation angle α2 of the rotor 214 at the instant when the end portion 212A of the cord 212 leaves the electrode 220. As a result, the detection of the rotation angle α2 can be made precise thereby improving the measurement precision of the residual torsion.

In the present embodiment, the electrodes 220 and 222 are formed in a rod shape, and there is provided the cover 230 for ensuring contact of the end portion 212A of the cord 212 with the electrodes 220 and 222 so that it is difficult for the electrodes 220 and 222 to separate from the end portion 212A of the cord 212 during the measurement. As a result, it is possible to ensure that the measurement of the residual torsion is appropriately carried out.

In the present embodiment, on the other hand, when the S-shaped switch 228A disposed in the operation portion 228 is pushed, for example, the clockwise rotation in the residual torsion is indicated by "+", and the counterclockwise rotation is indicated by "−". When the Z-shaped switch 228B is pushed, the counter-clockwise rotation is indicated by "+", and the clockwise rotation is indicated by "−". In accordance with the cord 212, therefore, the ± indications of the residual torsion can be precisely made.

In the present embodiment, on the other hand, by operating the switch 228C disposed in the operation unit 228, the rotating speed of the rotor 214 can be made to change in accordance with the diameter, material and so on of the cord 212. By setting the optimum rotating speed of the rotor 214 according to the diameter, material and so on of the cord 212, it is possible to ensure the measurement of the residual torsion and to shorten the measurement time.

By attaching the guide unit 248 to the upper portion of the residual torsion measuring apparatus 210, the cord 212 can be prevented from being affected by the straightness of the cord 212 and from moving during the measurement in the direction perpendicular to the axial direction, so that the measurement precision of the residual torsion can be better improved.

In the present embodiment, the end portion 212A of the cord 212 can be bent to the specified angle by the bending unit 260 before the start of measurement so that the measurement preparations can be automated.

Figure 16:
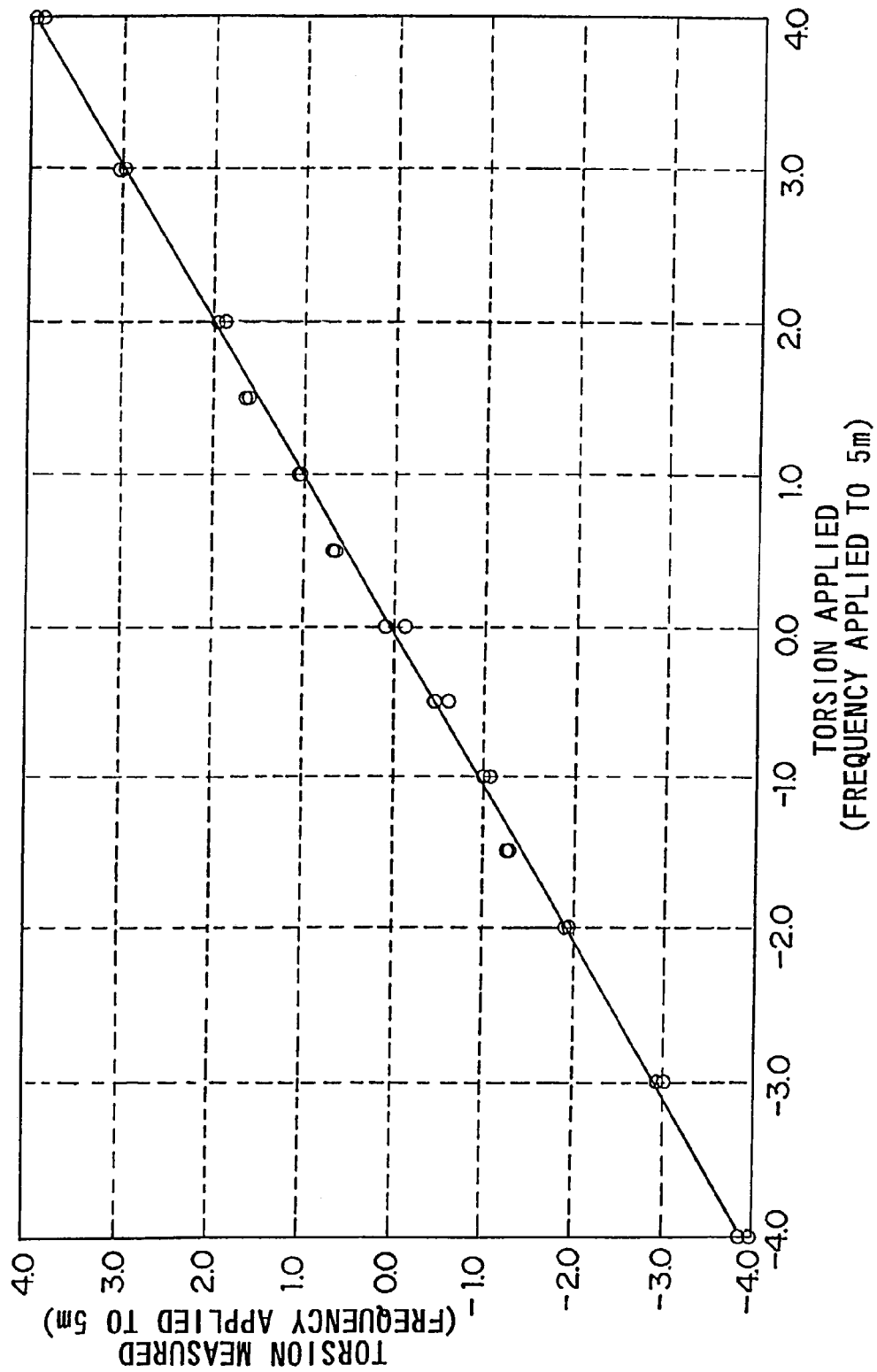
FIG. 16 is a diagram plotting the measured results of the residual torsion.

FIG. 16 is a graph plotting the results (by symbol O) which were obtained by applying a predetermined torsion to the cord 212 of 5 m and by measuring the torsion twice with the residual torsion measuring apparatus 210 of the present embodiment. From this graph, it is found that the values of the residual torsion measured in the present embodiment were hardly different from the applied torsion.

In the foregoing, specific embodiments of the present invention have been described in detail. It should, however, be apparent to those skilled in the art that the present invention should not be limited to those embodiments and could be embodied in other various manners within the scope thereof. For example, the present invention could be constructed such that the residual torsion measuring apparatus 210 has only one electrode 220 or 222.

Further, the operation portion 228 may be modified into another construction such as a touch panel, and the display means should not be limited to the display 226 but another display means such as a digital meter may be used. Further, the bending unit 260 may also be provided with the guide unit 248.

What is claimed is:

1. A straightness measuring apparatus comprising:
   first, second and third coordinate sensors for detecting three different coordinates along the longitudinal direction of an object to be measured as said first, second and third sensors are moved perpendicular to the longitudinal direction of the object to be measured;
   straightness computing means for computing the straightness of said object from the curvature of a curve passing through the three points detected by said first, second and third coordinate sensors;
   display means for displaying the result of the computations made by said straightness computing means; and
   a measurement plate for mounting the object thereon for said coordinate detection.

2. The apparatus of claim 1, wherein each of said first, second and third coordinate comprises a transparent type optical fiber sensor.

3. A straightness measuring apparatus comprising:
   first, second and third coordinate sensors for detecting three different coordinates along the longitudinal direction of an object to be measured as said first, second and third sensors are moved perpendicular to the longitudinal direction of the object to be measured;
   straightness computing means for computing the straightness of said object from the curvature of a curve passing through the three points detected by said first, second and third coordinate sensors;
   display means for displaying the result of the computations made by said straightness computing means; and
   sampling means for cutting the object to a predetermined length.

* * * * *